(12) United States Patent
Brelivet (10) Patent No.: US 8,561,376 B2
(45) Date of Patent: Oct. 22, 2013

(54) DEVICE FOR DISPENSING A PRODUCT IN A PETRI DISH

(75) Inventor: Nicolas Brelivet, Saint Jouan De L'isle (FR)

(73) Assignee: AES Chemunex, Combourg (FR)

( * ) Notice: Subject to any disclaimer, the term of this patent is extended or adjusted under 35 U.S.C. 154(b) by 329 days.

(21) Appl. No.: 13/132,510

(22) PCT Filed: Nov. 23, 2009

(86) PCT No.: PCT/EP2009/065625
§ 371 (c)(1),
(2), (4) Date: Jun. 2, 2011

(87) PCT Pub. No.: WO2010/066562
PCT Pub. Date: Jun. 17, 2010

(65) Prior Publication Data
US 2011/0243814 A1 Oct. 6, 2011

(30) Foreign Application Priority Data
Dec. 10, 2008 (FR) ...................................... 08 58437

(51) Int. Cl.
*B65B 5/10* (2006.01)
*B01L 99/00* (2010.01)

(52) U.S. Cl.
USPC ................ 53/250; 53/281; 53/310; 53/381.4; 141/82; 141/130

(58) Field of Classification Search
USPC ........... 53/168, 249, 250, 253, 281, 310, 311, 53/306, 381.4; 221/222, 231; 141/82, 130; 422/509
See application file for complete search history.

(56) References Cited

U.S. PATENT DOCUMENTS

| 2,865,156 | A | * | 12/1958 | Wolfson ......................... 53/237 |
| 2,987,163 | A |   | 6/1961 | Eddison et al. |
| 3,031,819 | A | * | 5/1962 | Menolasino et al. ........... 53/237 |
| 3,050,915 | A | * | 8/1962 | Silverstolpe ................ 53/111 R |
| 3,522,631 | A | * | 8/1970 | Niclas ............................ 425/162 |
| 3,704,568 | A |   | 12/1972 | Duhring et al. |
| 3,704,768 | A |   | 12/1972 | Hirozawa et al. |
| 3,719,023 | A | * | 3/1973 | Richardson .................. 53/381.4 |
| 3,844,896 | A |   | 10/1974 | Sharpe |
| 4,170,861 | A |   | 10/1979 | Snyder et al. |
| 4,468,914 | A |   | 9/1984 | Pestes |

(Continued)

FOREIGN PATENT DOCUMENTS

| DE | 197 50 912 | 5/1999 |
| FR | 2 789 693 | 8/2000 |

(Continued)

Primary Examiner — Hemant M Desai
(74) Attorney, Agent, or Firm — Harness, Dickey & Pierce, P.L.C.

(57) ABSTRACT

The disclosure relates to a device for dispensing a prescribed product in a Petri dish, the device comprising pistons, a transfer member with lid-bearing openings and a dish bottom, and a dispensor. According to the disclosure, the transfer member is a shuttle capable of translation relative to the base according to a direct reciprocating movement of the bearing openings between either of first and second stop positions, the dispensor being arranged so as to dispense the product above the inner opening and under the upper opening at the bottom of the dish when the openings are in a position selected from the first and second stop positions.

10 Claims, 11 Drawing Sheets

(56) References Cited

U.S. PATENT DOCUMENTS

| | | |
|---|---|---|
| 5,020,297 A | 6/1991 | Borie et al. |
| 5,476,362 A * | 12/1995 | Kobak et al. ............... 414/797.7 |
| 5,698,260 A | 12/1997 | Roth et al. |
| 5,787,687 A | 8/1998 | Mueller et al. |
| 6,199,605 B1 | 3/2001 | Inaba et al. |
| 6,560,946 B2 | 5/2003 | Orange et al. |
| 7,105,338 B1 | 9/2006 | Holmes et al. |
| 8,408,860 B2 * | 4/2013 | Gupta et al. .................. 414/411 |
| 2012/0277905 A1 * | 11/2012 | Botma et al. .................. 700/236 |

FOREIGN PATENT DOCUMENTS

| | | |
|---|---|---|
| FR | 2 789 694 | 8/2000 |
| GB | 886795 | 1/1962 |
| JP | 30-49676 | 6/1998 |
| JP | 2003-225083 | 8/2003 |

* cited by examiner

DEVICE FOR DISPENSING A PRODUCT IN A PETRI DISH

CROSS-REFERENCE TO RELATED APPLICATIONS

This application is a National Phase Entry of International Application No. PCT/EP2009/065625, filed on Nov. 23, 2009, which claims priority to French Patent Application Serial No. 0858437, filed on Dec. 10, 2008, both of which are incorporated by reference herein.

BACKGROUND AND SUMMARY

The invention concerns a device for dispensing a prescribed product, agar in particular, into Petri dishes.

Petri dishes are small dishes of circular contour, in transparent plastic material, which contain a nutrient such as an agar medium; they serve as medium for the development of cultures containing micro-organisms and are used in large number by analytical laboratories, in particular for medical research and in industry. A dispensing device is known for example from document EP-B-385 902. This device comprises a rotating tray which, successively and step by step, brings open Petri dishes with their lid held distant above the bottom part, from a station supplying empty dishes to a filling station, then from this filling station to a receiving station of filled dishes, this tray comprising two coaxial, circular horizontal plates which are superimposed, each pierced with a series of corresponding circular openings, the openings of the upper plate having a smaller diameter than the lids but slightly larger than the diameter of the bottom parts to allow passing of the bottom parts whilst retaining the lids, a piston being provided to transfer an empty dish on the tray by placing its bottom part in the lower plate and retaining its lid in the upper plate, and another piston being provided to lift the filled bottom part from the bottom plate up into the lid retained in the upper plate.

This device has numerous drawbacks. The dish filling rate is of the order of one dish every 6 seconds according to the indication given in the document, which is relatively low. In addition, the opening time for each Petri dish is relatively long (about 16 seconds for a tray rotating by one notch every 4 seconds). Therefore, the risk of polluting the inside of the dish with undesirable particles is high.

Finally, in order to be able to fill the greatest possible number of dishes in minimum time, the device is relatively tall which generates access difficulties at the top of carousel for loading the stacks of empty dishes and removing the stacks of filled dishes. This problem is all the more detrimental since the persons using the device are mostly women who statistically are shorter than men.

Document FR-A-2 433 752 describes a device in which the Petri dishes are unstacked from the lower part of carousel towards a rotating tray with two superimposed plates. This rotating tray comprises three stations: a Petri dish unstacking station, a filling station via a tube and an elevating station using elevating means to move a filled dish up towards another stack of the carousel. This device also has the above-mentioned disadvantages.

Linear conveying devices are also known. U.S. Pat. No. 3,704,768 describes a Petri dish filling device comprising a conveyor performing a linear movement under a stack of empty Petri dishes towards a fixed part comprising two upper rails spaced apart by a smaller distance than two lower rails, the conveyor comprising a upper tray and a lower tray. In this device, a Petri dish is brought from the stack on the upper tray. Then, after recoiling leftwards, the tray is translated towards the right so that the upper rails retain the lid and the bottom of the dish falls onto the lower rails. Filling of the open bottom part is then carried out. Next, a forward vertical surface of the conveyor pushes the lid and filled bottom part to the left beyond the upper rails to cause the lid to fall onto the bottom part and push the dish onto a receiving table.

This device does not therefore produce stacks of filled Petri dishes, and the user must stack up the filled dishes. Also, the empty dishes must come up against a hook to lift off the lid during translation on the conveyor, which exerts an abutment force on the dishes and might cause damage thereto. Each filled dish arrives on a receiving table distant by a distance equal to the widths of three dishes relative to the stack of empty dishes. This device is therefore additionally very bulky.

Other linear, endless-belt conveyor devices are known from documents U.S. Pat. Nos. 4,468,914 and 5,698,260. These devices are even bulkier.

The invention sets out to obtain a device which overcomes the above-mentioned disadvantages by means of a device supplying a stack of filled Petri dishes from a stack of empty Petri dishes, which is of small bulk, which is able to provide a fast filling rate and has a large dish capacity whilst avoiding or reducing the risks of contamination of the dishes when they are opened.

For this purpose, a first subject matter of the invention is a device for dispensing a prescribed product into at least one Petri dish, each Petri dish comprising a removable lid able to be placed over a bottom part of smaller width than the lid, the device—on a base—comprising:

at least first and second columns for vertical guiding of the Petri dishes, capable of respectively receiving first and second stacks of Petri dishes with lids placed over the bottom parts and capable of being respectively positioned above a first lower passageway for Petri dishes and above a second lower passageway for Petri dishes, the first and second passageways being provided on a fixed part relative to the base,     a system to move at least one Petri dish from the first column to the second column, comprising:

a transfer member having an upper opening supporting the lid of a Petri dish above a second lower opening supporting the bottom part of a Petri dish,         dispensing means to dispense said product above the lower opening into the bottom part of the Petri dish underneath the upper opening,         the mobile transfer member being capable of taking up a first stop position in which the supporting openings lie underneath the first passageway, and a second stop position in which the supporting openings lie underneath the second passageway,         a first piston comprising a first tray located under the first passageway and capable of passing through the openings to cause lowering of the lid and the bottom part of a Petri dish from the first column onto their respective supporting openings when the transfer member lies in the associated first stop position,         a second piston comprising a second tray located underneath the second lower passageway and capable of passing through the openings to raise the lid and the bottom part of the Petri dish from their respective supporting openings into the second column, when the transfer member lies in the associated second stop position, wherein:

the transfer member is a shuttle which moves in translation relative to the base, with direct back and forth movement of the supporting openings between each of the first and second stop positions, the dispensing means being arranged to dispense said product above the lower opening and underneath the upper opening into the bottom part of the dish when these openings lie in a selected one of the first and second stop positions. With the invention no time is lost in bringing an open dish to a product filling station.

In Embodiments of the Invention:

The device comprises synchronous driving means to drive the pistons to the same height.

The pistons are driven by the same motor.

The device comprises means for coordinating the translational movements of the shuttle and pistons so as to place them successively in the following positions:

the first stop position with a lowered position of the first tray under the lower opening, to bring the lid of the dish onto the upper opening and to bring the bottom part of the dish onto the lower opening, the second stop position, with the first tray under the lower opening for dispensing of product into the bottom part of the open dish positioned in the lower opening by the dispensing means, in the second stop position, an elevation position lifting the second tray into the second column to close the lid over the bottom part of the dish and to transfer this closed dish to the second column, the first stop position with a lowered position of the first tray underneath the lower opening.

The dispensing means comprise an outlet nozzle for the said product, means for displacing the dispensing nozzle being provided to cause it to move between one and the other of a dispensing position of the said product in which the nozzle lies above the lower opening and under the upper opening in said selected stop position, and a retracted position in which the nozzle no longer lies between the openings, control means being provided to allow movement of the piston associated with the selected stop position only when the nozzle is in retracted position.

In addition to said supporting upper and lower openings, called second openings, the shuttle comprises means to support the bottom part of the Petri dishes which are provided with a first opening allowing the passing of the first piston in the first stop position.

In addition to said supporting upper and lower openings, called second openings, the shuttle comprises first upper and lower openings, the shuttle comprises a top-plate and an bottom-plate spaced apart by a prescribed distance to form a passageway for the dispensing means in dispensing position, the bottom-plate comprising the first lower opening—for passing of the first tray and first piston—and said second lower opening supporting the bottom part of the dish, the top-plate comprising a first upper opening—for passing of the first tray and first piston—and said second upper opening supporting the lid, the first upper opening being located above the first lower opening.

The device comprises means for raising the first tray and first piston to above the shuttle, the first tray is fixed to at least one lower rod linking the first tray with said lifting means, the shuttle comprises at least one communication passageway between the second openings and the first opening or first openings to allow the passing of said lower supporting rod when the shuttle is moved between the stop positions and the first tray is in raised position above the shuttle.

The device comprises at least one carousel mounted in rotation on a vertical axis of the base, the carousel comprising a plurality of columns for vertical guiding of the Petri dishes and each capable of receiving a stack of Petri dishes with lid placed on the bottom part, means for driving the carousel in rotation being provided to bring two of the columns respectively above the first lower passageway for the Petri dishes and above the second lower passageway to form said first and second columns.

The device comprises means for retaining and releasing the passing of Petri dishes above the second passageway, these retaining and releasing means being mobile between a first retaining position of the Petri dishes above the second passageway in the second column, and a second release position to allow passing of the Petri dishes in the second passageway, constraining means to constrain to the first retaining position being provided, means being provided for lifting the second tray and second piston as far as a prescribed elevation position in the second column, the retaining means being arranged to be actuated in the second release position by abutment against said lid of the Petri dish when the second tray of the second piston carrying the dish of the associated lid is raised as far as the prescribed elevation position in the second column, the retaining means, in the first retaining position, forming a passageway width that is narrower than the width of the bottom part of the Petri dish to give support thereto but which is wider than the width of the second tray of the second piston to allow its lowering under the second column.

BRIEF DESCRIPTION OF THE DRAWINGS

The invention will be better understood on reading the following description given solely by way of non-limiting example, with reference to the appended drawings in which.

DETAILED DESCRIPTION

In the figures, the dispensing device 1 comprises a base 2 in the form of a box-type structure for example. The base 2 comprises a front face 22 on which there is a control panel of the device provided with a monitoring screen 4 for example and one or more control buttons 5 or any other interface 5 enabling the user to control the automatic functioning of the device 1. Means 6 are provided on the box structure for dispensing a prescribed product which may be liquid agar for example or an agar medium. These dispensing means 6 are in the form of a rotating head 6 for example rotating about a vertical axis on an upper face 21 of the box structure 2, the head 6 comprising a nozzle 61 as product outlet. These dispensing means 6 are supplied with product by tubing 7 connected to means 8 for feeding the product towards the dispensing means 6, these means 8 being formed for example of a peristaltic pump 8 arranged on the base 2 e.g. on the front face 22 thereof, the other end of the tubing 7 being connected to a reserve 9 of the product.

Figure 4A:
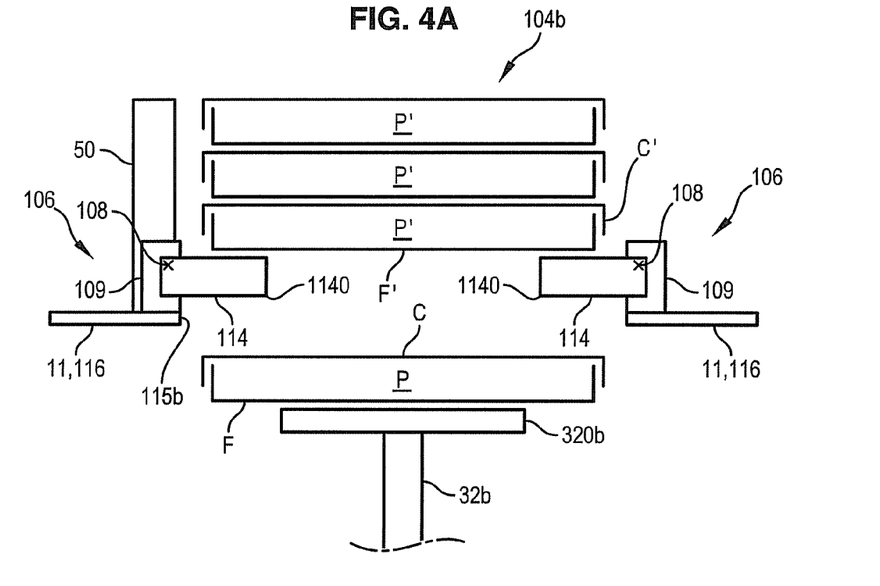
FIGS. 4A, 4B, 4C and 4D are schematic profile views of part of the device shown FIG. 1, in different positions.

The base 2 comprises an upper part 23 that is raised relative to the upper side face 21 adjacent this upper part 23. The raised part 23 carries a carousel storing Petri dishes. The carousel 10 is unique on the base 2 and can rotate relative to a central vertical axis 101 on part 23 of the base 2. The carousel 10 comprises a lower ring 102 carrying means 103 for storing Petri dishes in stacks. These means 103 delimit a plurality of vertical columns 104 for housing and guiding stacks of Petri dishes, and for this purpose they comprise rods 103 or any other vertical guiding means for the Petri dishes. A removable upper ring 107 is provided for capping the means 103. Each column 104 opens downwards via an opening 105 for passing of a Petri dish in the lower ring 102. Therefore these openings 105 have a larger diameter than the diameter of the Petri dishes. The openings 105 of the columns 104 are distributed equidistant from the central rotation axis 101 and equi-angularly on the lower ring 102. The openings 105 are peripheral to the lower ring 102 for example and in the form of cut-outs of the ring 102. The height of the guiding means 103 is designed for the receiving in each column 104 of a stack of several Petri dishes in a prescribed number up as far as the ring 107. Each Petri dish P is placed in the column 104 with its lid C arranged on its bottom part F so that the dish is removably closed, Petri dishes in manner known per se having a lid C that is wider than their bottom part F as is illustrated FIGS. 4A and 4B. When the Petri dish is closed, the rim of the lid lies outside the rim of the bottom part.

Under the lower ring 102 of the carousel and on the base 2 there is a plate 11 for horizontal guiding of the Petri dishes when they are in the carousel 10. The axis 101 of the carousel is connected to rotational driving means located in the base 2 to cause the carousel 10 to rotate horizontally about this vertical axis 101. The horizontal guiding plate 11 is fixed to the raised part 23 and comprises a part 116 located above the upper surface 21 and underneath several columns 104 of the carousel 10. The horizontal guiding plate 11, at part 116, comprises a first opening or passageway 115a and a second opening or passageway 115b having the same spatial arrangement as two lower openings 105 of the carousel 10, to allow the passing of a Petri dish through these openings 105, 115a, 115b. For greater compactness, the distance between the first opening 115a and the second opening 115b of plate 105 corresponds to the distance between two first and second respective adjacent lower openings 105a and 105b of the carousel 10.

The first and second openings 115a and 115b of the plate 11 lie above a station 20 allowing the unstacking of empty Petri dishes, the opening thereof, the dispensing of product into their bottom part, the closing thereof and their re-stacking in the filled state. The station 20 is located on the upper face 21 of the base 2. The station 20 comprises a system 30 for moving the Petri dishes one by one in the empty state from underneath the column 104b into the opening 105b through opening 115a, via a transfer member 31 in horizontal translation and via two first and second vertically displaced pistons 32a, 32b under the second and first columns 104a, 104b respectively. Each piston 32a, 32b comprises an upper tray 320a, 320b fixed to a lower vertical rod 321a, 321b linked in the base 2 to vertical displacement driving means for lowering and raising the pistons 22a, 22b. According to the invention, the transfer member 31 is a shuttle 31 moving back and forth in translation along a longitudinal horizontal direction X.

One embodiment of the member 31 is illustrated FIG. 2 and is described in more detail below. In this embodiment, as illustrated FIGS. 3A, 3B, 3C, 3D, 3E, 3F ad 3G, the pistons 32a and 32b have simultaneous vertical translation movements, so that their trays 320a, 320b lie at the same height with respect to each other. In this case, this allows the providing of only one motor for driving both pistons 32a and 32b in vertical translation. In the illustrated embodiment, the first and second pistons 32a and 32b have the same movement, in synchronism, and lie at the same time in the top position (FIGS. 3A and 3G), bottom position (FIGS. 3B, 3C, 3D) or elevation position (FIGS. 3E, 3F).

The shuttle 31 comprises a top-plate 311 and a bottom-plate 312 secured to one another by spacers 313. Evidently, the shuttle 31 may be made in a single piece. The bottom-plate 312 is used to guide the shuttle 31 in translation on the surface 21, and to ensure the stability of shuttle 31 on this surface 21. The means 60 for driving the shuttle 31 in translation are lateral and housed in the base 2 underneath the raised part 23.

In the figures, the top-plate 311 comprises a first upper opening 311a and a second upper opening 311b which are respectively located above a first lower opening 312a and a second lower opening 312b of the bottom-plate 312. The first lower and upper openings 311a and 312a are used for passing of the first tray 320a of the first piston 32a and are wider than the latter. The second upper opening 311b is used for passing of the bottom part F of a Petri dish and for retaining the lid C of a Petri dish. The second upper opening 311b has a width Lb larger than that of the bottom part F of a Petri dish, but smaller than that of its lid C. The second lower opening 312b is used to give support to the bottom part F of a Petri dish and its width is smaller than the width of this bottom part F. The second openings 311b and 312b are therefore called supporting openings for a Petri dish P.

In addition, the top-plate 311 comprises a connecting passageway 311c between the first upper openings 311a and the second upper opening 311b to allow passing of the rod 321a of the first piston 32a between these openings 311a and 311b. The passageway 311c has a transverse horizontal width that is greater than that of the rod 321a of the first piston 32a. The bottom-plate 312 comprises a connecting passageway 312c between the first lower opening 312a and the second lower opening 312b to allow passing of the rod 321a of the first piston 32a between these openings 311a and 311b. The passageway 312c has a transverse horizontal width that is greater than that of the rod 321a of the first piston 32a.

Figure 2:
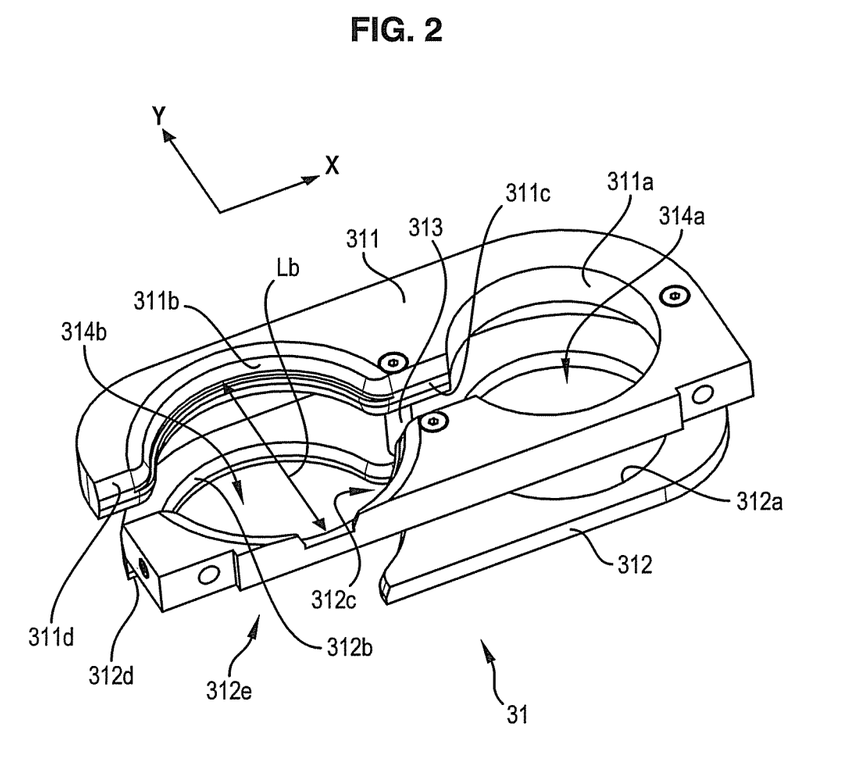
FIG. 2 is a perspective, schematic view of part of the device shown FIG. 1.

In FIG. 2, the shuttle 31 extends in the longitudinal horizontal direction X which is the horizontal direction extending between the two openings 115a and 115b of the plate 105. The transverse horizontal direction Y is the direction perpendicular to the longitudinal direction X.

The plate 11 comprises means 106 for retaining and releasing the passing of Petri dishes P, P' stacked above the second opening 115b. These means 106 are mobile between a first retaining position of a stack of Petri dishes P' via the underside thereof above the opening 115b in column 104b as illustrated FIGS. 4A, 4C and 4D, and a second release position to allow passing of the Petri dishes in the opening 115b as is illustrated FIG. 4B. These Petri dishes P' already located in the column 104b comprise a lid C' placed over a bottom part F'. The means 106 for example, at several points around the opening 115b, comprise a lug 114 hinged on a horizontal rotation pin 108 on a support 109 fixed to the part 116 in the vicinity of the opening 115b, for example two diametrically opposite lugs 114. In the retained position in FIGS. 3B, 3C, 3D and 4A, the lugs 114 extend above the opening 115b to delimit between them a width that is smaller than the width of the bottom part F' of the Petri dishes P' so as to support the bottom part F' of the lowermost dish, this width allowing passing of the tray 320*b* of piston 32*b* between the lugs 114 and being wider than the width of this tray 320*b*.

Figure 4B:
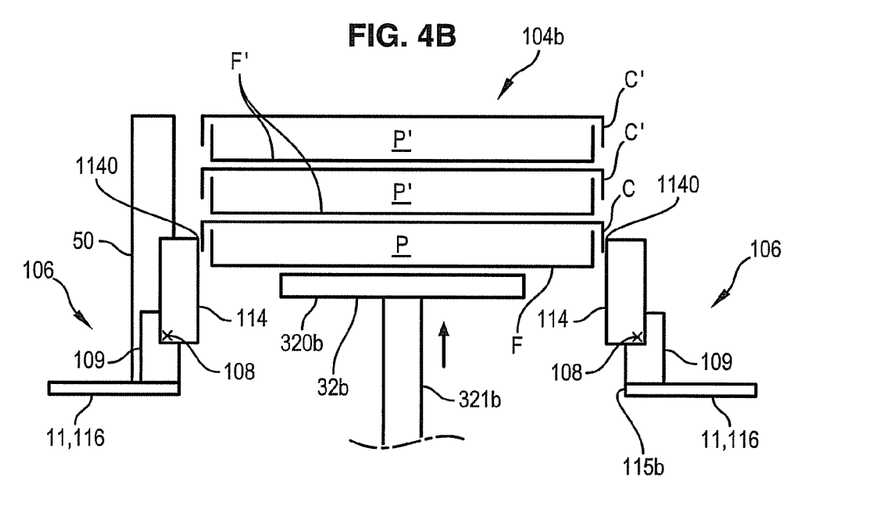

When the tray 320*b*, carrying a Petri dish P with its lid C placed over its bottom part F, passes from bottom to top through the opening 115*b* towards the column 104*b* in FIG. 4B, the lid C of this dish B, lifted by the tray 320*b*, lifts the lugs 114 to cause them turn outwardly. During the rising of the tray 320*b* in FIG. 4B, the tray 320*b* is at a height relative to the opening 115*b* such that the lugs 114 via their free end 1140 distant from the pin 108 bear laterally against the Petri dishes P, P'. Means are provided to urge the lugs 114 to be applied towards the retaining position, for example under gravity or through the positionning of their pin 108 in the lug 114 or via a spring or other positive return means.

Figure 3E:
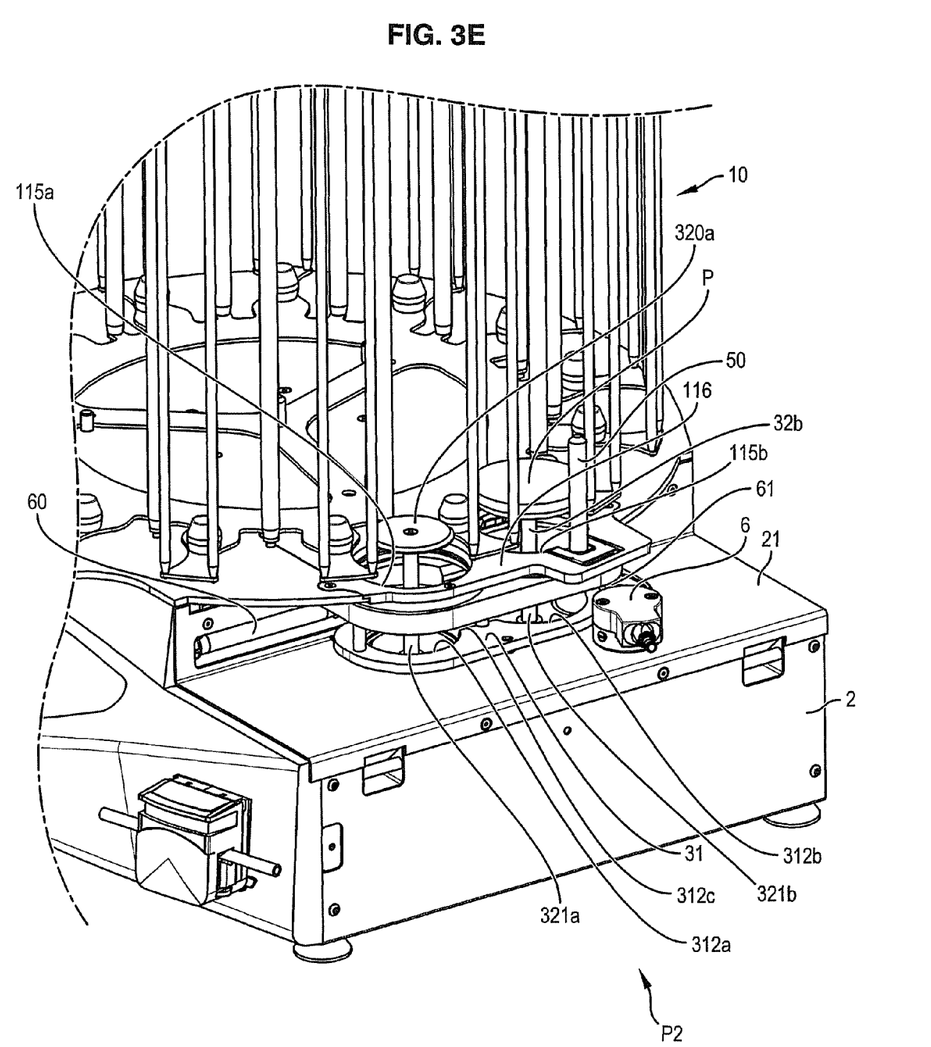
Figure 3F:
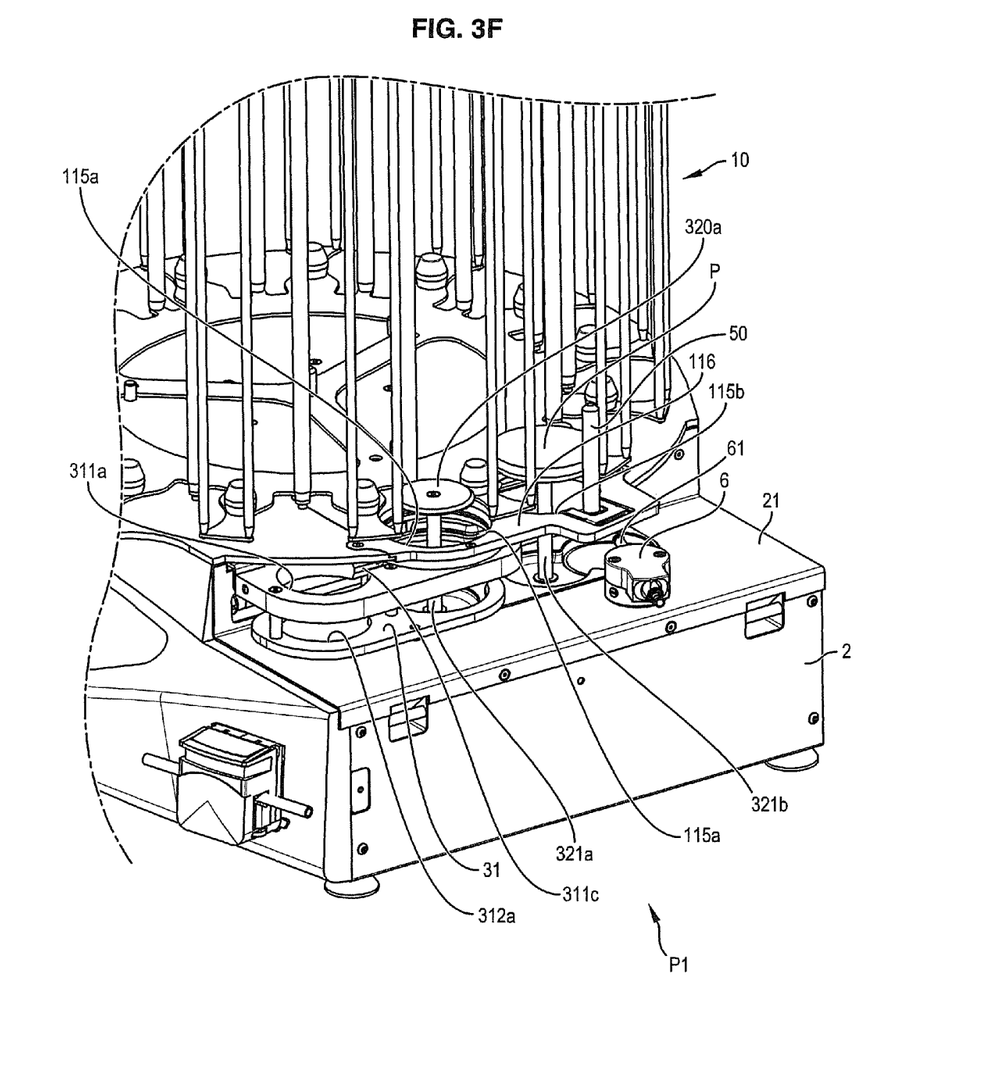
Figure 4C:
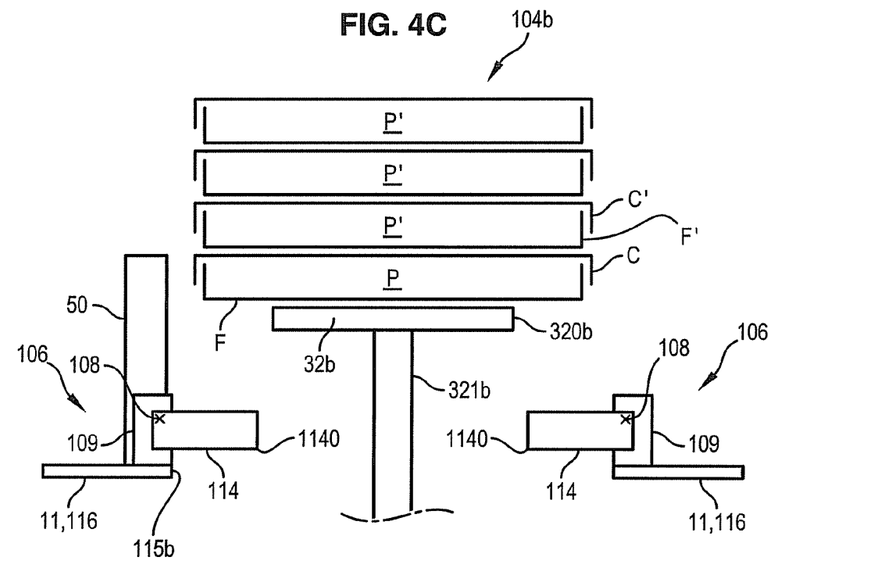

In FIG. 4C, the tray 320*b* moves into an elevation position above the free end 1140 which had been bearing against the dishes P, P' supported by the tray. This elevation position corresponds to FIGS. 3E and 3F. Therefore, the end 1140 of the lugs falls back into the retaining position towards the opening 115*b*. When, from FIG. 4C to FIG. 4D, the piston 32*b* is lowered, its tray 320*b* passes between the lugs 114 lying in retaining position, and then passes through the opening 115*b*, which deposits the stack of Petri dishes P, P' on the lugs 114 in retaining position.

The functioning of the device is as follows. FIGS. 3A, 3B, 3C, 3D, 3E, 3F and 3G illustrate the pathway of an empty Petri dish i.e. comprising a lid C and bottom part F, which is the lowermost dish at the bottom of column 104*a*. In FIGS. 3A, 3B, 3F and 3G the shuttle 31 lies in a first stop position. In FIGS. 3C, 3D and 3E, the shuttle 31 lies in a second stop position.

In the first stop position P1, the supporting openings 311*b* and 312*b* of the shuttle 31 are positioned below the first opening 115*a*, which itself is positioned under an opening 105*a* of a column 104*a* of empty, closed Petri dishes. In the first stop position P1, the shuttle 31 is arranged on the other side of the second piston 32*b*, a solid part 117 of the plate 11 being inter-positioned between the carousel 10 and the first upper opening 311*a* of the shuttle 31.

In the second stop position P2, the first openings 311*a* and 312*a* of the shuttle 31 are positioned underneath the first opening 115*a* and underneath the first column 104*a*. In the second stop position, the second openings 311*b* and 312*b* of the shuttle 31 lie underneath the second opening 115*b* and underneath the second column 104*b*. In the embodiment shown in the figures, the shuttle 31, as stop positions, solely comprises the first stop position P1 and the second stop position P2.

Figure 3A:
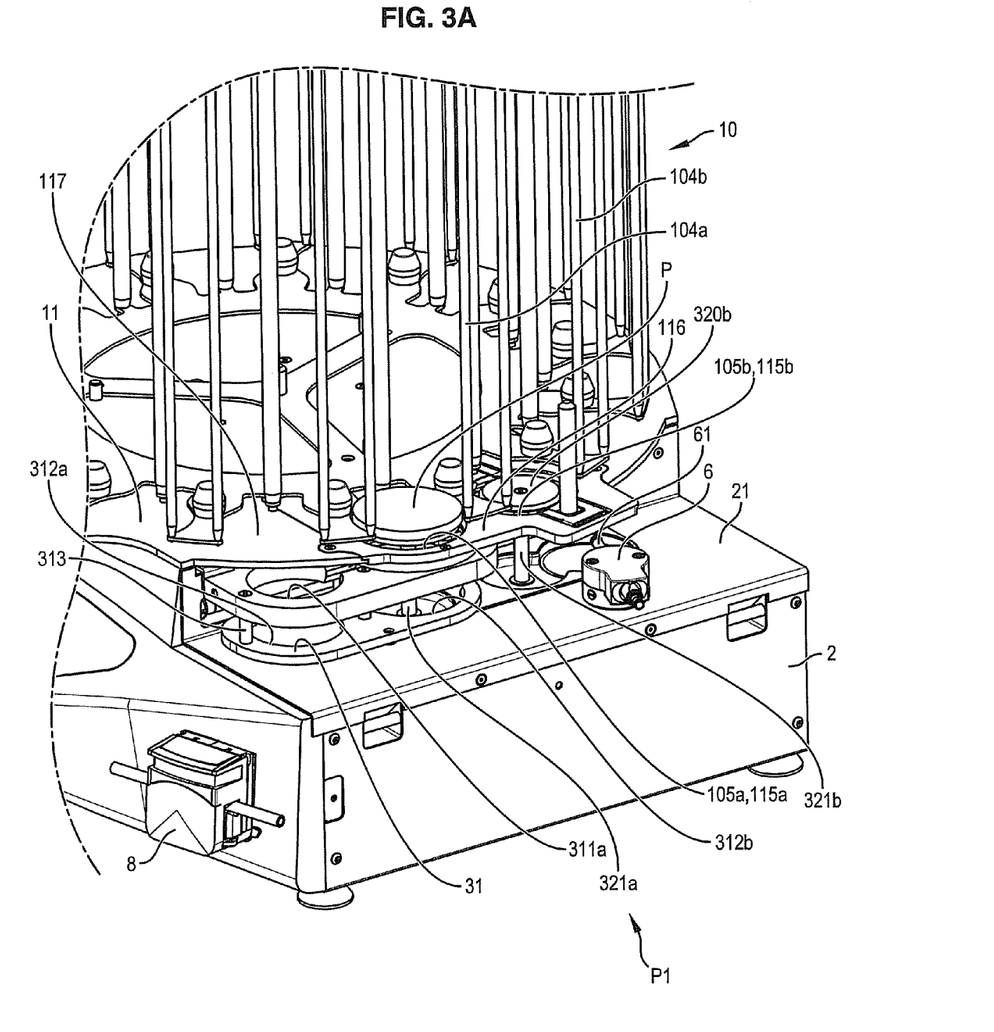
FIGS. 3A, 3B, 3C, 3D, 3E, 3F and 3G are magnified partial views of the device shown FIG. 1, in different successive operating positions for the filling of a Petri dish.
Figure 3B:
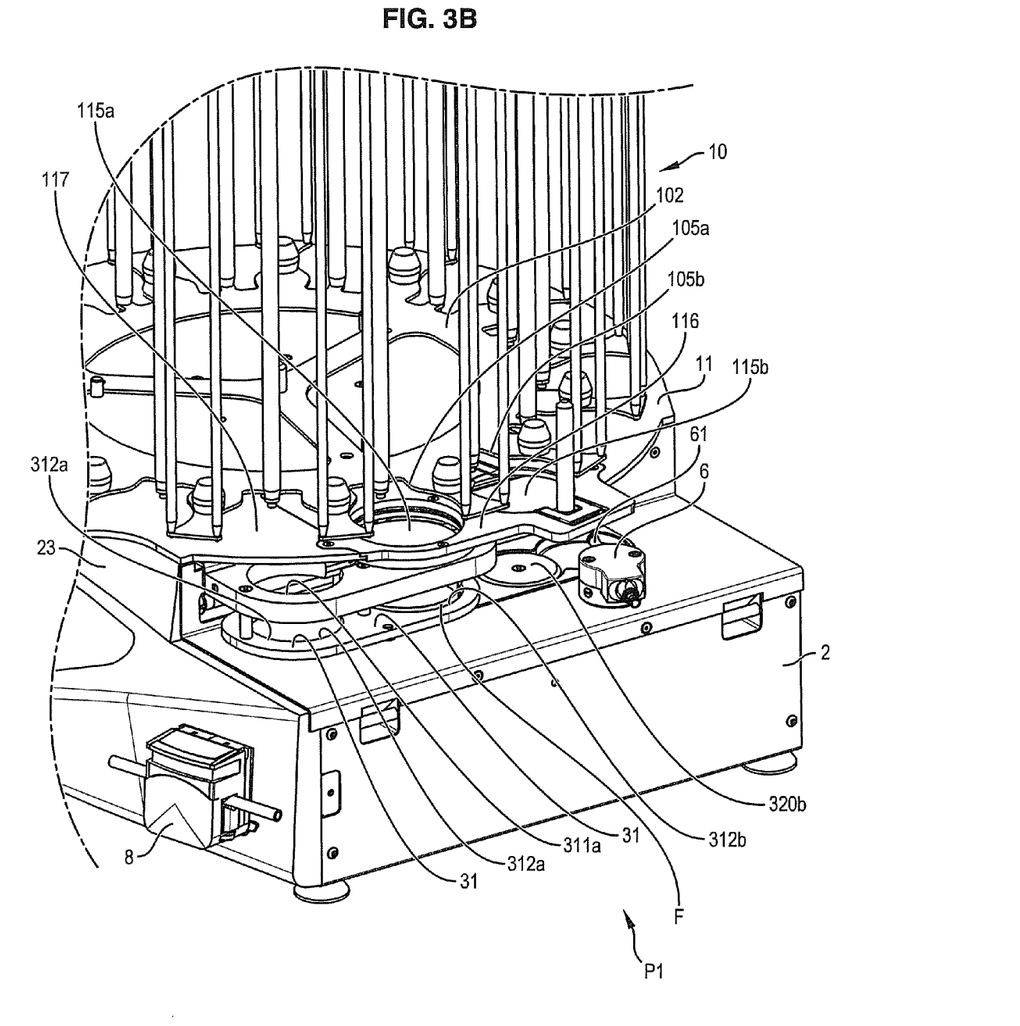
Figure 3C:
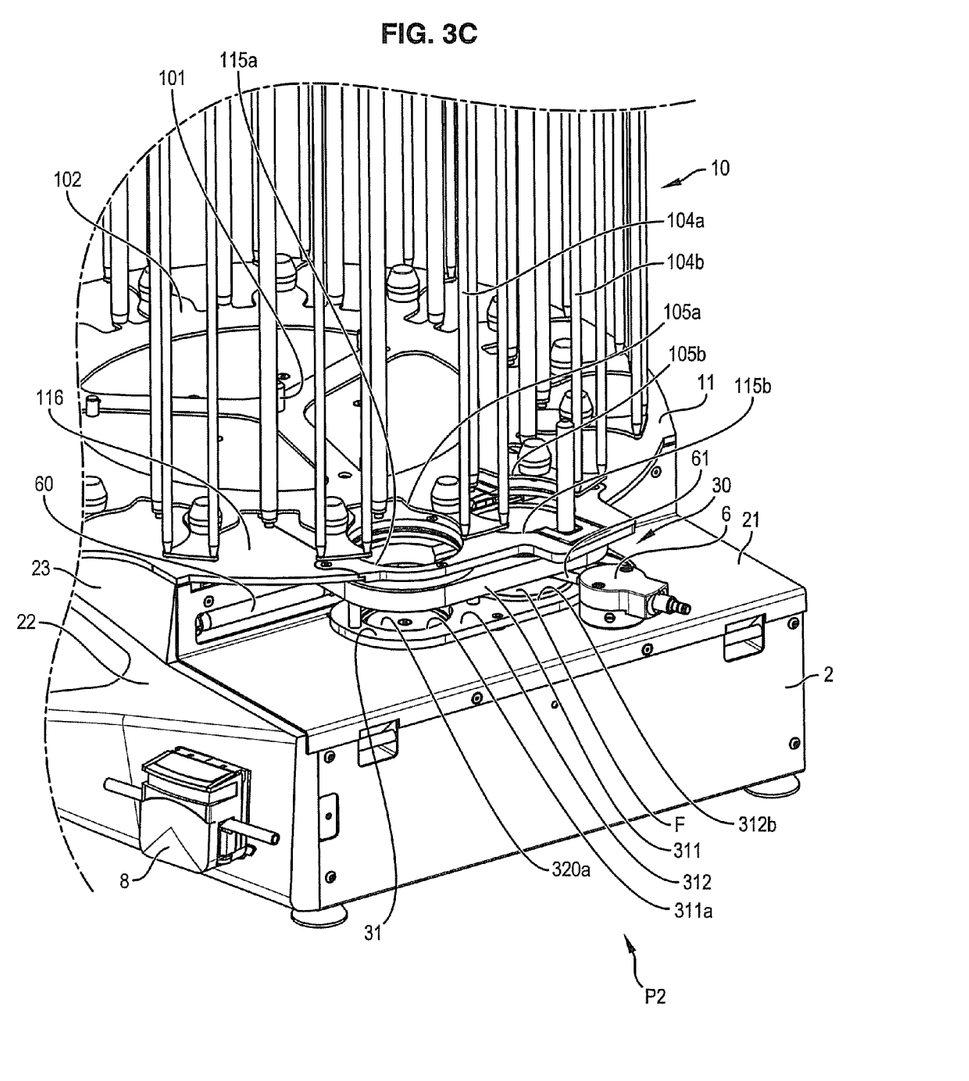
Figure 3D:
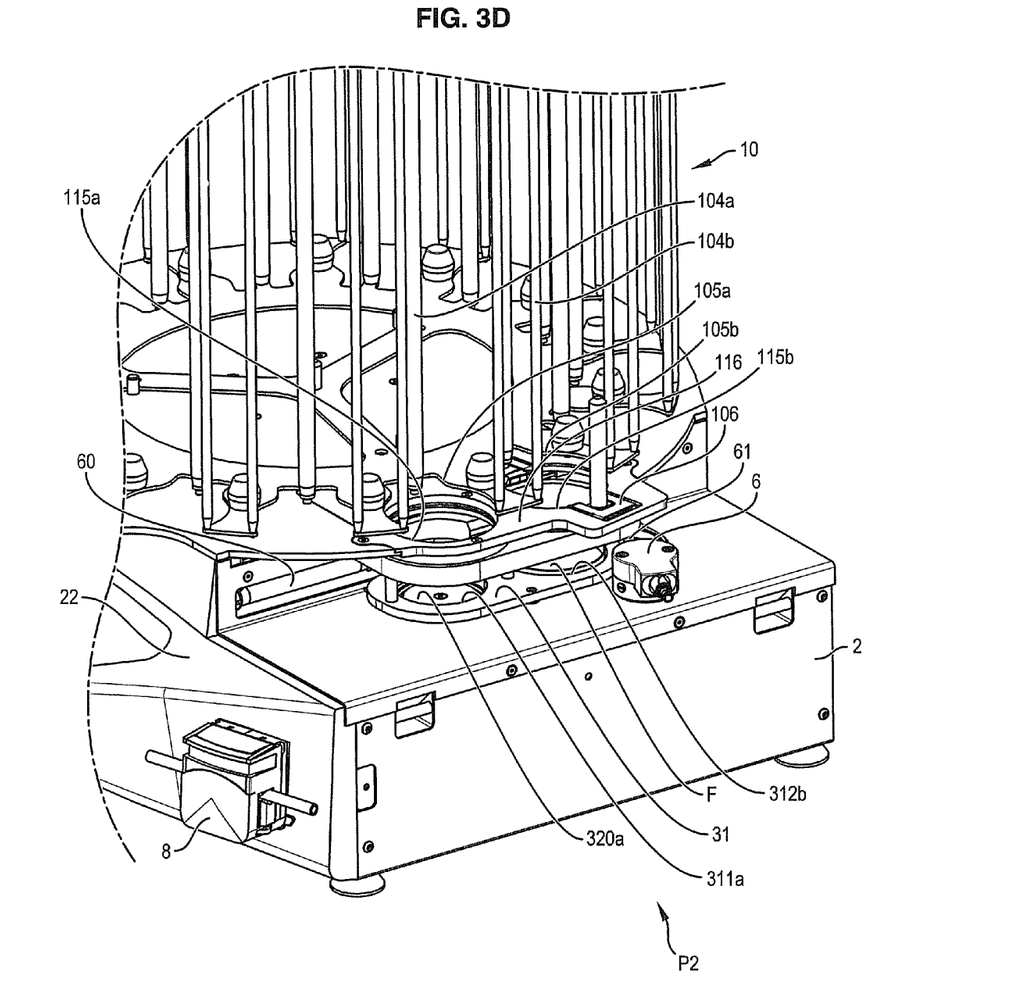

In FIG. 3A, the first tray 320*a* of the first piston 32*a* supports the first stack 104*a* of Petri dishes P in the first column 104*a* above the second openings 312*b* and 311b, the rod 321*a* passing through these openings 312*b* and 311*b*. The piston 32*a* is then lowered through second openings 311 b and 312*b* of the shuttle 31 to bring the lid C of the lowermost Petri dish P at the bottom of the column 104*a* onto the second upper opening 311*b* and bring the bottom part F of the Petri dish onto the second lower opening 312*b*, to arrive at the position shown FIG. 3B. In FIGS. 3B, 3C, 3D the trays 310*a*, 320*b* of the pistons are positioned underneath the shuttle 31, for example in housings arranged in the surface 21.

In FIGS. 3A and 3B, the means 6 for dispensing the product are in a retracted position in which the nozzle 61 lies neither above the opening 312*b* nor above the piston 32*b*. In this retracted position, the nozzle 61 leaves the passageway clear between the second lower opening 312*b* and the second upper opening 311*b*, and in this case it lies outside the stroke of the piston 32*b*. The shuttle 31 is then moved by longitudinal horizontal translation along direction X to arrive at the second stop position shown FIG. 3C. The dispensing means 6 change over to a dispensing position to dispense the product, for example by rotation of the dispensing head 36 so as to bring its dispenser nozzle 61 between the top-plate 311 and bottom-plate 312 above the second lower opening 312*b* and hence above the bottom part F located therein as seen FIG. 3C.

The bottom part F supported on/in the second opening 312*b* and the lid C supported on/in the second upper opening 311*b* come to be positioned underneath the second opening 115*b* of the fixed plate 11 and under the second column 104*b*. Automatic means provided in the base 2 cause commanding of the feed means 8 to send product into the dispensing means 6, this product being dispensed by these means 6 above the second upper opening 312*b* into the bottom part F of the Petri dish located therein. Next, in the position illustrated FIG. 3D, the dispensing means return to their position away from the second lower opening 312*b*, or retracted position.

Then in FIG. 3E, the pistons 32*a* and 32*b* move to the elevation position in FIG. 4C above the shuttle 31 and in the column 104*b*. The second piston 32 first lifts the bottom part F positioned in the second lower opening 312*b*, then raises the bottom part F up into the lid C located in the second upper opening 311*b*, which closes the Petri dish P whose bottom part contains product which has been dispensed by the dispensing means, and then lifts the filled, closed dish P into the second column 104*b* through the second opening 115*b* and the second opening 104*b* of the carousel 10. The tray 320*b* therefore supports the filled, closed dish P in the column 104 and any other dishes P' which may already be inside the column 104*b*.

Next, in FIG. 3F, the shuttle 31 is translated to its first stop position corresponding to FIG. 3B. In FIG. 3F, the second openings 312*b* and 311*b* of the shuttle 31 are located under the first openings 115*a* and 104*a*, whilst the first openings 311*a* and 312*a* are located under the solid part 117 of the plate 11. During this translation movement, the rod 321*a* of the first piston 32*a* therefore moves from the second openings 311*b* and 312*b* to 311*a* and 312*a* crossing the passageways 311*c* and 312*c* arranged in the top-plate 311 and bottom-plate 312.

Figure 3G:
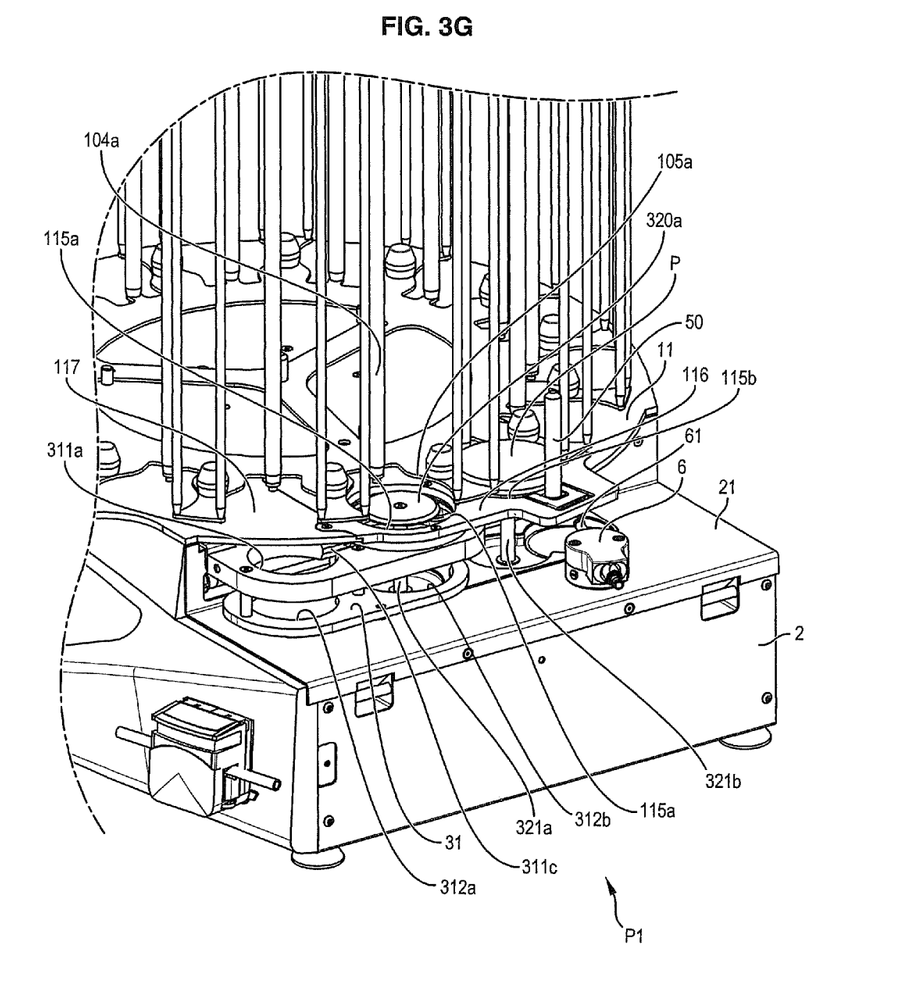
Figure 4D:
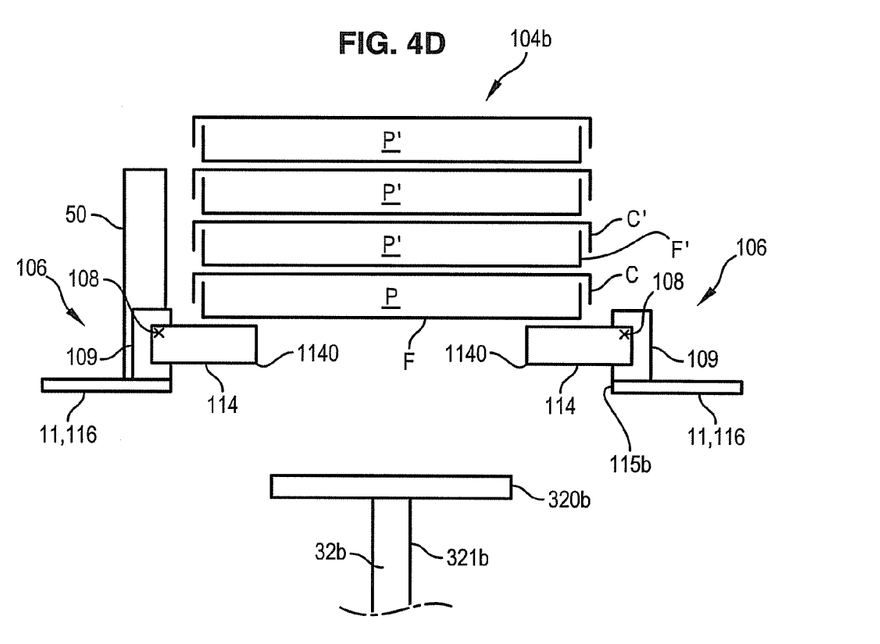

Next, in FIG. 3G, the trays 320*a* and 320*b* of the pistons return to a position lower than the elevation position shown FIG. 3F, this position in FIG. 3G corresponding to the one shown FIGS. 3A and 4D. In FIGS. 3A and 3G the Petri dishes of column 104*b* are supported by means 106. Means 50 for vertical guiding of the dishes P, P' in the second column 104*b* are fixed to the plate 11 in the vicinity of the opening 115*b* and comprise a vertical bar 50 for example to place the dishes P, P' in a straight stack during the rising and lowering of the second piston 32*b* in FIGS. 4A to 4D.

The bulk of the shuttle 31 is about that of two side-by-side Petri dishes, corresponding to its position underneath two adjacent columns 104 as in FIG. 3C. The travel distance of the shuttle 31, in the illustrated embodiment, corresponds to the distance between the two adjacent columns 104*a* and 104*b* of Petri dishes. The width of the first upper opening 311*a* is smaller than the width of the bottom part F of a Petri dish to support the stack of Petri dishes from the first column 104*a* when this first upper opening 311*a* lies thereunder as in FIGS. 3C and 3D.

Evidently, the shuttle 31 could have any shape other than the one illustrated in the figures, whilst still having a first vertical passageway 314*a* leading from the first lower opening 312*a* to the first upper opening 311*a* to allow displacement of the first tray 320*a* of the first piston 32*a* therein, a second vertical passageway 314b leading from the second lower opening 312b to the second upper opening 311b to allow passing of the first and second trays 320a and 320b of the first and second pistons 32a, and 32b, and the third upper passageway 311c between the upper openings 311b and 311a and the fourth lower passageway 312c between the lower openings 312a and 312b, it evidently being possible for these third and fourth passageways 311c and 311d to be only one. On account of the small bulk of the shuttle 31, it is possible to form a carousel 10 having a greater number of columns 104. Therefore, the number of Petri dishes P being equal, it is possible to obtain a carousel 10 of shorter height since the Petri dishes are distributed over a larger number of columns 104. The manufacture of the device is also simpler and cheaper.

For optimal use of the device, the user fills all the columns 104 of the carousel except one with stacks of empty Petri dishes. The column free of Petri dishes is brought by rotation of the carousel 10 to above the second opening 115b and above the tray 320b of the second piston 32b in FIG. 3A. The empty Petri dishes P derived from column 104a are then successively filled, following the above-described process.

Figure 1:
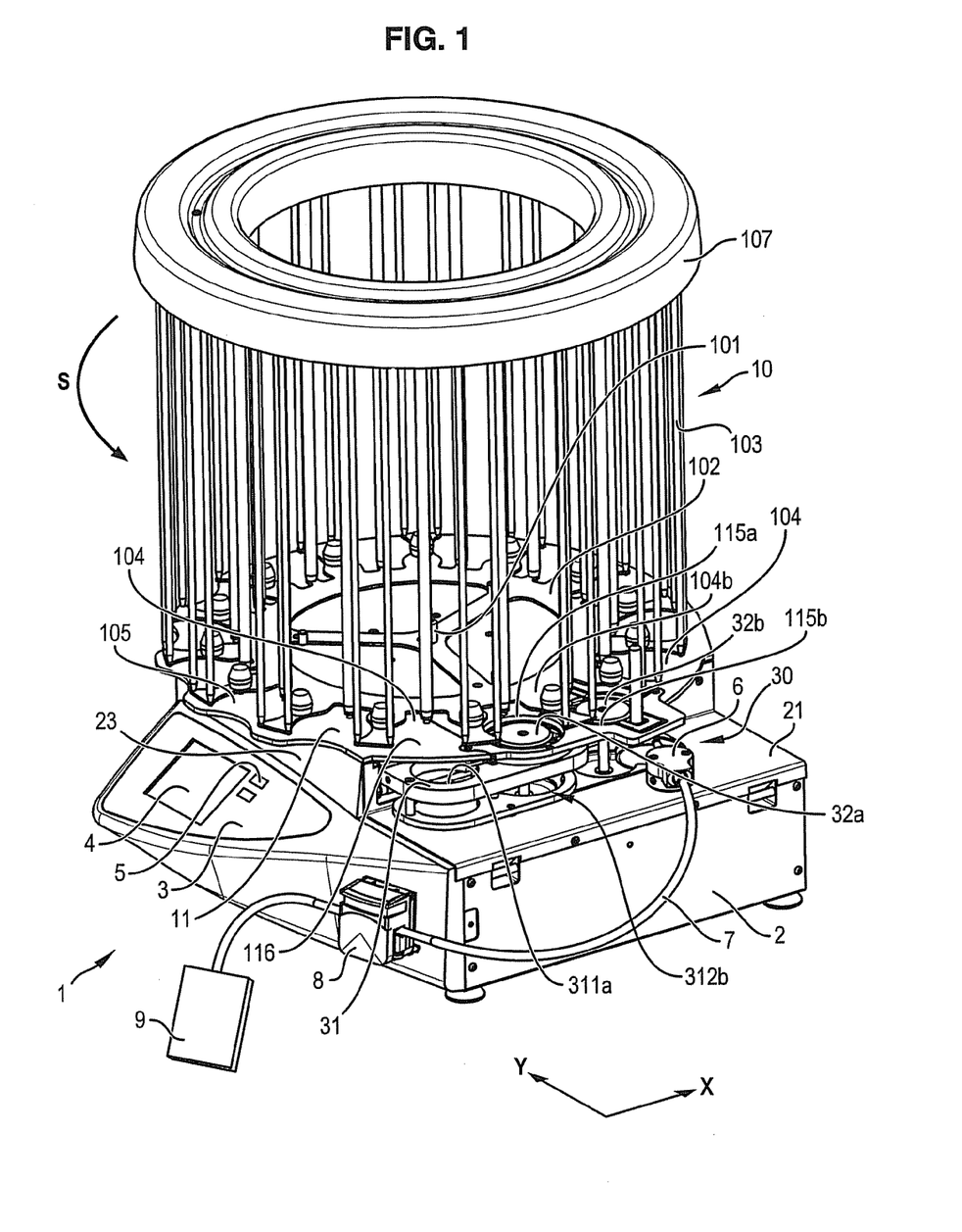
FIG. 1 is a perspective, schematic view of one embodiment of a machine using the dispensing device of the invention.

The filled Petri dishes P are transferred one after another into column 104b which initially did not contain any dish. When the column 104a positioned above the first opening 115a no longer contains any dishes P, the carousel 10 is rotated in direction S illustrated FIG. 1 to cause this new empty column to move to above the second opening 115b. This direction of travel S of the carousel by one column is the same direction from stop position P1 to stop position P2. In this case, a new column of empty Petri dishes, which was initially located on the solid part 112 of the plate 11, comes to lie above the first opening 115a for unstacking. The same process is repeated with this stack of dishes.

The shuttle 31 also comprises a longitudinal end passage for the rod 321b of the piston i.e. in the illustrated embodiment, a first upper longitudinal end passage 311d in the top-plate 311, opening firstly into the second upper opening 311b and secondly onto the outside in the longitudinal direction, and a lower longitudinal end passage 312d in the bottom-plate 312, causing the second lower opening 312b to communicate with the outside in the longitudinal direction. For example, in FIG. 2, the second lower opening 312b and the passage 312d are in the form of a cut-out of the bottom-plate 312 opening onto the lower longitudinal end and onto one side 312e.

A detector detecting the presence of a bottom part F in the second lower opening 312b can be provided. This detector may be fixed for example relative to the base 2, to detect the presence of a bottom part F in the second lower opening 312b at the first stop position and/or at the second stop position. Provision may therefore be made for a first detector under the first column 104a. Provision may also be made for another detector under the second column 104b. The process of filling Petri dishes P is carried out for as long as the detector gives information on the presence of a bottom part F of a dish in opening 312b. If the detector does not give any indication of the presence of a bottom part F in the opening 312b, the process is interrupted or the feeding of product into the dispensing means 6 is interrupted.

The control and coordination means to control the different means for driving the carrousel 10, pistons 32a and 32b and the shuttle 31 are automated and are actuated via the control interface 5. For example, these means may be provided in the form of a microprocessor in the base 2. The device of the invention is intended to be integrated in an automated Petri dish filling machine.

The invention claimed is:

1. A device for dispensing a prescribed product into at least one Petri dish, each Petri dish comprising a removable lid able to be arranged over a bottom part of smaller width than the lid, the device comprising on a base:
(a) at least first and second columns adapted to vertically guide the Petri dishes, respectively capable of receiving first and second stacks of Petri dishes with the lids placed over the bottom part and capable of being positioned respectively above a first lower passageway for the Petri dishes and above a second lower passageway for the Petri dishes, the first and second passageways being provided on a fixed part relative to the base;
(b) a system operably moving at least one of the Petri dishes from the first column to the second column, the system comprising:
a transfer member having an upper opening supporting the lid of
an associated one of the Petri dishes above a second lower opening supporting the bottom part of the associated Petri dish;
a dispensor operably dispensing the product above the lower opening into the bottom part of the associated Petri dish underneath the upper opening;
the mobile transfer member being capable of taking up a first stop position in which the supporting openings are located under the first passageway, and a second stop position in which the supporting openings are located under the second passageway;
a first piston comprising a first tray located under the first passageway and capable of passing through the openings, to lower the lid and the bottom part of the associated Petri dish in the first column onto their respective supporting openings when the transfer member lies in the associated first stop position;
a second piston comprising a second tray located under the second lower passageway and capable of passing through the openings to lift the lid and bottom part of the Petri dish from their respective supporting openings up into the second column when the transfer member lies in the associated second stop position;
the transfer member being a shuttle with translational movement relative to the base in direct back and forth movement of the supporting openings between each of the first and second stop positions; and
the dispensor being arranged to dispense the product above the lower opening and under the upper opening into the bottom part of the Petri dish when these openings lie in a selected one of the first and second stop positions.

2. The device according to claim 1, further comprising means for synchronous driving of the pistons at the same height.

3. The device according to claim 2, wherein the pistons are driven by the same motor.

4. The device according to claim 1, further comprising means for coordinating the translational movements of the shuttle and to place them successively in the following positions:
the first stop position with a lowered position of the first tray under the lower opening to bring the lid of the dish onto the upper opening and to bring the bottom of the dish onto the lower opening;
the second stop position with the first tray under the lower opening for dispensing of the product by the dispensor into the bottom part of the open dish located in the lower opening;

in the second stop position, an elevation position of the second tray in the second column to close the lid on the bottom of the dish and to transfer the closed dish to the second column; and the first stop position with a lowered position of the first tray under the lower opening.

5. The device according to claim 1, wherein the dispensor further comprises an outlet nozzle for the product, an actuator moving the dispensing nozzle between one and the other of a dispensing position of said product in which the nozzle lies above the lower opening and under the upper opening in the selected stop position, and a retracted position in which the nozzle no longer lies between the openings, and a controller provided so as only to allow movement of the piston associated with the selected stop position when the nozzle is in retracted position.

6. The device according to claim 1, wherein the shuttle, in addition to the upper and lower supporting openings called second openings, comprises a support operably supporting the bottom part of Petri dishes having a first opening to allow passing of the first piston in the first stop position.

7. The device according to claim 6, further comprising an actuator operably lifting the first tray of the first piston to above the shuttle, the first tray is fixed to at least one lower rod linking the first tray to the actuator, the shuttle comprises at least one passageway communicating the second openings with the first opening or first openings to allow passing of the lower supporting rod when the shuttle moves between the stop positions and the first tray is in raised position above the shuttle.

8. The device according to claim 1, wherein the shuttle, in addition to the upper and lower supporting openings called second openings, comprises first upper and lower openings, the shuttle comprises a bottom-plate and a top-plate spaced apart by a prescribed distance to arrange a passageway for the dispensor in the dispensing position, the bottom-plate comprising the first lower opening for passing of the first tray and of the first piston and said second lower opening supporting the bottom part of the dish, the top-plate comprising a first upper opening for passing of the first tray and of the first piston and the second upper opening supporting the lid, the first upper opening being positioned above the first lower opening.

9. The device according to claim 1, further comprising at least one carousel mounted in rotation on a vertical axis of the base, the carousel comprising a plurality of columns for vertical guiding of the Petri dishes and each capable of receiving a stack of the Petri dishes with the lids arranged over the bottom part, a driver operably driving the carousel in rotation being provided to bring two of the columns respectively above the first lower passageway for the Petri dishes and above the second lower passageway to form said first and second columns.

10. The device according to claim 1, further comprising:

means for retaining and passing Petri dishes above the second passageway, these retaining and passing means being mobile between a first retaining position of the Petri dishes above the second passageway in the second column, and a second release position allowing passing of the Petri dishes in the second passageway, provision being made for constraining means to constraint to the first retaining position;

means being provided for lifting the second tray of the second piston up to a prescribed elevation position in the second column;

the retaining means being arranged to be actuated in the second release position, by abutment against the lid of the Petri dish when the second tray of the second piston carrying the dish associated with the lid is lifted to the prescribed elevation position in the second column; and the retaining means forming a passageway in the first retaining position which is less wide than the width of the bottom part of the Petri dish to give support thereto and which is wider than the width of the second tray of the second piston to allow lowering thereof under the second column.

* * * * *